United States Patent [19]

Saikawa et al.

[11] 4,263,292
[45] Apr. 21, 1981

[54] 7-METHOXYCEPHALOSPORINS AND PHARMACEUTICAL COMPOSITION COMPRISING THE SAME

[75] Inventors: Isamu Saikawa; Shuntaro Takano; Hiroyuki Imaizumi; Isamu Takakura; Hirokazu Ochiai; Takashi Yasuda, all of Toyama; Hideo Taki, Tokyo; Masaru Tai; Yutaka Kodama, both of Toyama, all of Japan

[73] Assignee: Toyama Chemical Co., Ltd., Tokyo, Japan

[21] Appl. No.: 81,835

[22] Filed: Oct. 4, 1979

Related U.S. Application Data

[63] Continuation-in-part of Ser. No. 926,939, Jul. 21, 1978, abandoned.

[30] Foreign Application Priority Data

Jun. 13, 1978 [JP] Japan ................................. 53-70417
Apr. 23, 1979 [JP] Japan ................................. 54-49001
Aug. 7, 1979 [JP] Japan ................................. 54-99917

[51] Int. Cl.³ .................. A61K 31/545; C07D 501/57
[52] U.S. Cl. ....................................... 424/246; 544/21
[58] Field of Search ........................... 544/21; 424/246

[56] References Cited

U.S. PATENT DOCUMENTS 4,045,438  8/1977  Haviv et al. ............................ 544/21
4,087,424  5/1978  Saikawa et al. ........................ 424/246
4,103,008  7/1978  Toshiyasu ............................... 424/246
4,129,730  12/1978 Saikawa et al. ........................ 544/21

Primary Examiner—Paul M. Coughlan, Jr.
Attorney, Agent, or Firm—Oblon, Fisher, Spivak, McClelland & Maier

[57] ABSTRACT

A 7α-methoxycephalosporin represented by the general formula and a salt thereof:

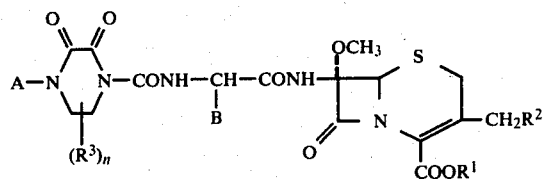

wherein $R^1$ represents a hydrogen atom or a carboxyl-protecting group; $R^2$ represents an organic group linked to the carbon atoms through an oxygen or sulfur atom; $R^3$ represents a lower alkyl group; n is 0, 1 or 2; A represents a hydrogen atom or a substituted or unsubstituted alkyl group; and B represents a substituted or unsubstituted alkyl group. These compounds have a broad antibacterial spectrum and high resistance to β-lactamase produced from bacteria, and are well absorbed in a living body.

16 Claims, No Drawings

7 α-METHOXYCEPHALOSPORINS AND PHARMACEUTICAL COMPOSITION COMPRISING THE SAME

CROSS-REFERENCES TO RELATED APPLICATION

This application is a continuation-in-part of application Ser. No. 926,939, filed on July 21, 1978 now abandoned.

This invention relates to novel 7α-methoxy-cephalosporins and pharmaceutical compositions comprising the same.

The compounds of this invention are characterized by having a broad antibacterial spectrum against Gram-positive and -negative bacteria, particularly having an excellent antibacterial activity against Gram-negative bacteria such as *Escherichia coil, Klebsiella pneumoniae,* Proteus species, *Serratia marcescens, Alkaligenes faecalis,* etc. and being stable to β-lactamase produced from bacteria. They are, therefore, very useful in treating various infectious diseases.

Although conventional 7α-methoxycephalosporins are known to have an antibacterial activity against Gram-positive bacteria, they have a relatively weak antibacterial activity against Gram-negative bacteria as mentioned above, which cause clinically serious infectious diseases.

The present inventors have conducted extensive research on 7α-methoxycephalosporins. As a result, it has been found that novel compounds represented by the general formula (I), described hereinafter, in which the cephem ring bears an organic-group-substituted oxy- or thio-methyl group at the 3-position and a methoxy group at the 7α-position, and the amino group at the 7β-position is linked to the group

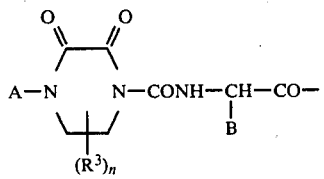

wherein $R^3$, n, A and B have the meanings described hereinafter, and salts of the compounds have effective antibacterial activity and low toxicity, and are well absorbed in a living body.

It is an object of this invention to provide novel 7α-methoxycephalosporins having in their molecule a 2,3-dioxo-1-piperazinecarbonylamido group and a group B.

It is another object of this invention to provide novel 7α-methoxycephalosporins having a broad antibacterial spectrum.

It is a further object of this invention to provide novel 7α-methoxycephalosporins having high resistance to β-lactamase produced from bacteria.

It is a still further object of this invention to provide novel 7α-methoxycephalosporins having an effective antibacterial activity against clinical isolates of bacteria.

It is a still further object of this invention to provide a process for producing the novel 7α-methoxy-cephalosporins.

It is a still further object of this invention to provide a pharmaceutical composition comprising the novel 7α-methoxycephalosporin or its salts as active ingredient.

Other objects and advantages of this invention will become apparent from the following description.

According to the present invention, there can be obtained the novel compound which includes 7α-methoxycephalosporins represented by the general formula (I), and salts thereof.

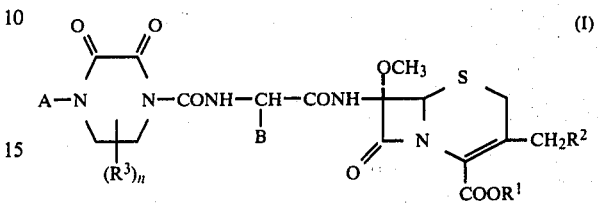

wherein $R^1$ represents a hydrogen atom or a carboxyl-protecting group; $R^2$ represents an organic group linked through an oxygen or sulfur atom; $R^3$ represents a lower alkyl group; n is 0, 1 or 2; A represents a hydrogen atom or a substituted or unsubstituted alkyl group; and B represents a substituted or unsubstituted alkyl group.

The term "alkyl" used herein means a straight or branched chain alkyl having 1 to 14 carbon atoms, such as methyl, ethyl, propyl, isopropyl, butyl, pentyl, hexyl, heptyl, octyl, dodecyl or the like; the term "lower alkyl" used herein means a straight chain alkyl having 1 to 4 carbon atoms, such as methyl, ethyl, propyl or butyl; the term "lower alkoxy" used herein means a monovalent -O-lower alkyl in which the lower alkyl defined above is bonded to oxygen, namely a straight chain alkoxy having 1 to 4 carbon atoms; the term "acyl" used herein means an acyl having 1 to 10 carbon atoms, such as acetyl, propionyl, butyryl, benzoyl, naphthoyl, pentanecarbonyl, cyclohexanecarbonyl, furoyl, thenoyl or the like; and the term "acyloxy" used herein means a monovalent -O-acyl in which the acyl defined above is bonded to oxygen, namely an acyloxy having 1 to 10 carbon atoms. When the term "acyl" and "acyloxy" means those having a heterocyclic ring containing N, O and/or S in any number in any position of the ring, the hetero atom or atoms being calculated as carbon atoms in melting the definition given above.

In the general formulas described herein, $R^1$ is a hydrogen atom or a carboxyl-protecting group. The carboxyl-protecting groups in this invention are those which have conventionally been used in the penicillin and cephalosporin fields and include ester-forming groups which can be removed by catalytic reduction, chemical reduction or other treatments under mild conditions; ester-forming groups which can easily be removed in living bodies; and other known ester-forming groups which can easily be removed by treatment with water or an alcohol, such as organic silyl groups, organic phosphorus-containing groups, organic tin-containing groups, or the like.

Examples of suitable carboxyl-protecting groups are:
(a) Alkyl groups:
(b) Substituted lower alkyl groups, at least one of the substituents of which is chloro, bromo, fluoro, nitro, carboalkoxy, acyl, lower alkoxy, oxo, cyano, lower alkylthio, lower alkylsulfinyl, lower alkylsulfonyl, lower alkoxycarbonyl, 1-indanyl, 2-indanyl, furyl, pyridyl, 4-imidazolyl, phthalimido, acetidino, aziridino, pyrrolidinyl, piperidino, morpholino, thiomorpholino, N-lower-alkylpiperazino, 2,5-dimethylpyrrolidinyl, 1,4,5,6-tetrahydropyrimidinyl, 4-methylpiperidino, 2,6-dimethylpiperidino, lower alkylamino, di-lower-alkylamino, acyloxy, acylamino, di-lower-alkylaminocarbonyl, lower alkoxycarbonylamino, lower alkoxycarbonyloxy, or lower alkylanilino or lower alkylanilino substituted by chloro, bromo, lower alkyl, or lower alkoxy;

(c) Cycloalkyl groups containing 3 to 7 carbon atoms, lower-alkyl-substituted $C_{3-7}$cycloalkyl groups, or [2,2-di(lower alkyl)-1,3-dioxolan-4-yl]methyl groups;

(d) Alkenyl groups containing up to 10 carbon atoms;

(e) Alkinyl groups containing up to 10 carbon atoms;

(f) Phenyl group, substituted phenyl groups, at least one of the substituents of which is one selected from the substituents exemplified in above (b); or aryl groups represented by the formula;

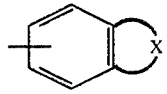

wherein X is —CH=CH—O—, —CH=CH—S—, —CH$_2$CH$_2$S—, —CH=N—CH—N—, —CH=CH—CH=CH—, —CO—CH=CH—CO—, or —CO—CO—CH=CH—, or substituted derivatives thereof, the substituents of which are ones selected from those exemplified in above (b), or the formula:

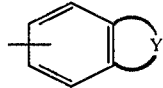

wherein Y is a lower alkylene group such as —(CH$_2$)$_3$— and —(CH$_2$)$_4$—, or substituted derivatives thereof, the substituents of which are ones selected from those exemplified in above (b);

(g) Aralkyl groups such as benzyl group or substituted benzyl groups, at least one of the substituents of which is one selected from those exemplified in above (b);

(h) Heterocyclic groups such as furyl, quinolyl, methyl-substituted quinolyl, phenazinyl, 1,3-benzodioxolanyl, 3-(2-methyl-4-pyrrolinyl), 3-(4-pyrrolinyl) and N-(methyl-pyridyl), or substituted heterocyclic groups, at least one of the substituents of which is one selected from those exemplified in above (b);

(i) Alicyclic indanyl or phthalidyl groups or substituted derivatives thereof, the substituent of which is methyl, chloro, bromo or fluoro; alicyclic tetrahydronaphthyl group or its substituted derivative, the substituent of which is methyl, chloro, bromo or fluoro, trityl group, cholesteryl group, and bicyclo-[4,4,0]-decyl group.

The carboxyl-protecting group listed above are typical examples, and there may be used any groups selected from those disclosed in U.S. Pat. Nos. 3,499,909; 3,573,296; and 3,641,018, West German Offenlegungsschrift Nos. 2,301,014; 2,253,287; and 2,337,105.

In the general formulas, $R^2$ is "an organic" group linked through an oxygen or sulfur atom". Examples of $R^2$ are lower alkoxy groups; lower alkylthio groups; acyloxy groups; carbamoyloxy group; and heterocyclic thio groups containing O, S and N alone or in any combination in any position, such as oxazolylthio, thiazolylthio, isoxazolylthio, isothiazolylthio, imidazolylthio, pyrazolylthio, pyridylthio, pyrazinylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzthiazolylthio, triazolopyridylthio, purinylthio, pyridine-1-oxide-2-ylthio, and the like.

Further, the above-mentioned $R^2$ groups may be substituted by a halogen atom or a lower alkyl, phenyl, $C_{2-5}$alkenyl, hydroxyl, lower alkoxy, lower alkylthio, nitro, cyano, lower alkylamino, di-lower-alkylamino acylamino, acyl, acyloxy, acyl-lower alkyl, carboxyl, carbamoyl, amino-lower alkyl, N-lower-alkylamino-lower-alkyl, N,N-di-lower-alkyl-amino-lower-alkyl, hydroxy-lower-alkyl, hydroxyimino-lower-alkyl, lower-alkoxy-lower-alkyl, carboxy-lower-alkyl, sulfo-lower-alkyl, sulfo, sulfamoyl-lower-alkyl, sulfamoyl, carbamoyl-lower-alkyl, carbamoyl-$C_{2-5}$-alkenyl, N-hydroxycarbamoyl-lower-alkyl or the like.

In the general formulas, A is a hydrogen atom or a substituted or unsubstituted alkyl group. Examples of the said alkyl group are as exemplified in the definition of alkyl hereinbefore. Examples of substituents of the substituted alkyl groups for group A include halogen atoms, lower alkoxy groups, cyano group, nitro group, carboxyl group, lower alkoxycarbonyl groups, hydroxyl group, lower alkylthio groups, acyl groups, N,N-disubstituted amino groups, and the like.

In the general formulas, B is a substituted or unsubstituted alkyl group. Examples of the said alkyl group are as exemplified in the definition of alkyl hereinbefore. The substituents borne by the alkyl groups represented by B include halogen atoms, hydroxyl group, protected hydroxyl groups, acyl groups, mercapto group, lower alkylthio groups, nitro group, amino group, protected amino groups, imino group, protected imino groups, carboxyl group and the like.

The protecting groups of the above-mentioned protected amino and imino groups include all groups which can usually be used as amino-protecting groups, such as easily removable groups such as, for example, trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenyl sulfenyl, acetyl, chloroacetyl, trifluoroacetyl, formyl, tert.-butoxycarbonyl, p-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-yl-methoxycarbonyl, 2-pyridylmethoxycarbonyl, 2-furyloxycarbonyl, diphenylmethoxycarbonyl, 1,1,-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like; and other easily removable amino-protecting groups, for example, trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, di- or tri-alkylsilyl, and the like.

The protecting groups of the above-mentioned protected hydroxyl groups include all groups which can usually be used as hydroxyl-protecting groups, for example, lower alkyl, α-ethoxyethyl, benzyl, benzhydryl, tetrahydrofuryl, tetrahydropyranyl, organic silyl, such as di- or tri-lower alkylsilyl, di- or tri-lower alkoxysilyl, diphenylmethylsilyl and the like, and substituted or unsubstituted acyl, alkoxycarbonyl or aralkoxycarbonyl, exemplified as amino-protecting group mentioned above.

The salt of the 7α-methoxycephalosporin of this invention represented by the general formula (I) includes those formed at the acidic group and those formed at the basic group, which are well known in the penicillin and cephalosporin fields. Of the salts, pharmaceutically acceptable salts are preferred. The salts formed at the acidic group include salts with alkali metals such as sodium, potassium and the like; alkaline earth metals such as calcium, magnesium and the like; ammonium; and nitrogen-containing organic bases such as procaine, dibenzylamine, N-benzyl-β-phenethylamine, 1-ephenamine, N,N-dibenzylethylenediamine, trimethylamine, triethylamine, tributylamine, pyridine, dimethylaniline, N-methylpiperidine, N-methylmorpholine, diethylamine, and dicyclohexylamine.

The salts formed at the basic group include salts with mineral acids such as hydrochloric acid, sulfuric acid and the like; organic carboxylic acids such as oxalic acid, formic acid, trichloroacetic acid, trifluoroacetic acid and the like; and organic sulfonic acids such as methanesulfonic acid, toluenesulfonic acid, naphthalenesulfonic acid, and the like.

All optical isomers and racemic compounds, and all crystal forms and hydrates of the 7α-methoxycephalosporin represented by the general formula (I) and salt thereof are included within the scope of this invention.

The compounds represented by the general formula (I) or salts thereof are produced by the known methods such as, for example, those described below.

Production method (1): A method by which a compound of the general formula (II):

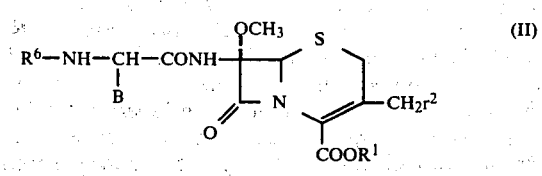

wherein $R^6$ represents a hydrogen atom, an organic silyl group or organic phosphorus-containing group; and $R^1$, $R^2$ and B have the same meanings as defined above, is reacted with a reactive derivative in the carboxyl group of a compound represented by the general formula (III):

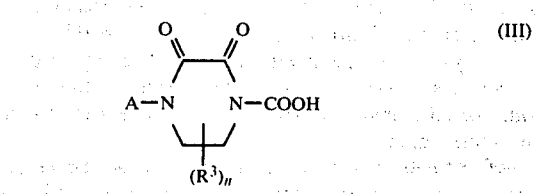

wherein $R^3$, n and A have the same meanings as defined above.

Production method (2): A method by which a compound of the general formula (IV):

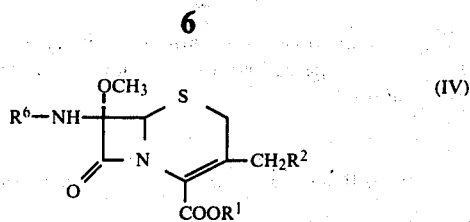

wherein $R^1$, $R^2$ and $R^6$ have the same meanings as defined above, is reacted with a compound represented by the general formula (V):

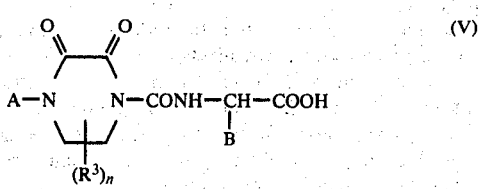

wherein $R^3$, n, A and B have the same meanings as defined above or a reactive derivative in the carboxyl group of said compound (V).

Production method (3): A method by which a cephalosporin of the general formula (VI):

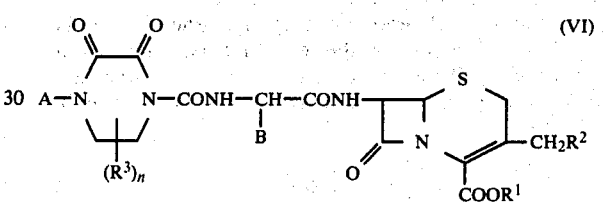

wherein $R^1$, $R^2$, $R^3$, n, A and B have the same meanings as defined above, is reacted, in the presence of methanol, with an alkali metal methylate represented by the general formula (VII):

wherein $M^1$ represents an alkali metal, and then reacted with a halogenating agent.

Production method (4): A method by which a 7α-methoxycephalosporin of the general formula (VIII):

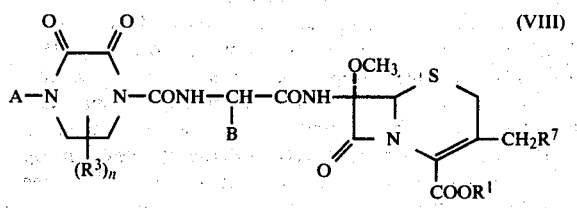

wherein $R^7$ represents a group easily replaceable by a nucleophilic reagent; and $R^1$, $R^3$, n, A and B have the same meanings as defined above, is reacted with a compound represented by the general formula (IX):

wherein $M^2$ represents a hydrogen atom, an alkali metal or an alkaline earth metal, and $R^2$ has the same meaning as defined above.

The organic silyl groups and the organic phosphorus-containing groups represented by $R^6$ in the above-mentioned general formulas include those groups which are conventionally used as amino- or carboxyl-protecting group in the penicillin and cephalosporin synthesis fields, such as

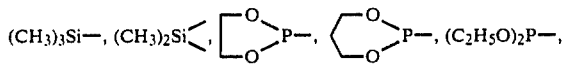

and (C₂H₅)₂P—, which are easily removed by treatment with, for example, water or an alcohol.

The groups represented by R⁷, which are easily replaceable by a nucleophilic reagent, include halogen atoms such as chlorine, bromine and the like; lower alkanoyloxy groups such as formyloxy, acetoxy, propionyloxy, butyryloxy, pivaloyloxy and the like; arylcarbonyloxy groups such as benzoyloxy, naphthoyloxy and the like; arylthiocarbonyloxy groups such as thiobenzoyloxy, thionaphthoxyloxy and the like; arylcarbonylthio groups such as benzoylthio, naphthoylthio and the like; arylthiocarbonylthio groups such as thiobenzoylthio, thionaphthoylthio and the like; carbamoyloxy group; thiocarbamoyloxy group; pyridine-N-oxide-2-yl group; and pyridazine-N-oxide-6-yl group. These groups represented by R⁷ may further contain substituents such as, for example, a halogen atom, nitro group, lower alkyl group, lower alkoxy group, lower alkylthio group, acyl group and the like.

The compound represented by the general formula (V) is easily obtained by the reaction between an alkali metal salt, an alkaline earth metal salt or an organic base salt of a compound represented by the general formula (X):

wherein B has the same meaning as defined above, and a reactive derivative in the carboxyl group of a compound represented by the general formula (III) in the presence of an acid-binding agent in an inert solvent.

The compounds represented by the general formulas (II) and (IV) may be synthesized in a manner known per se, for example, the manner described in the Journal of Synthetic Organic Chemistry, Japan Vol. 35, 568–574 (1977).

The modes of practice of the production methods (1), (2), (3) and (4) are described below.

The methods (1) and (2) can be carried out under nearly the same conditions. The compound (II) or (IV) is dissolved or suspended in an inert solvent such as, for example, water, acetone, tetrahydrofuran, dioxane, acetonitrile, dimethylformamide, dimethylacetamide, methanol, ethanol, methoxyethanol, diethyl ether, diisopropyl ether, benzene, toluene, methylene chloride, chloroform, ethyl acetate, or methyl isobutyl ketone, each alone or in admixture of two or more. To the resulting solution or suspension is added a reactive derivative in the carboxyl group of the compound (III), or the compound (V) or a reactive derivative in the carboxyl group of the compound (V). The mixture is allowed to react in the presence or absence of a base at −60° to 80° C., preferably −40° to 30° C. A reaction time of 5 minutes to 5 hours is generally sufficient.

The bases used in the above reaction include inorganic bases such as alkali metal hydroxides, alkali metal hydrogen carbonates, alkali metal carbonates and alkali metal acetates; tertiary amines such as trimethylamine, triethylamine, tributylamine, pyridine, N-methylpiperidine, N-methylmorpholine, lutidine, collidine and the like; and secondary amines such as dicyclohexylamine, diethylamine and the like.

When the compound (V) or a salt thereof is used in the method (2) as the starting material, the reaction can be carried out in the presence of a dehydrating-condensing agent such as, for example, N,N'-dicyclohexylcarbodiimide, N-cyclohexyl-N'-morpholinoethylcarbodiimide, N,N'-diethylcarbodiimide, N,N'-carbonyl bis(2-methylimidazole), trialkyl phosphites, ethyl polyphosphate, phosphorus oxychloride, phosphorus trichloride, 2-chloro-1,3,2-dioxaphospholane, oxalyl chloride, dimethylchloroforminium chloride, and dimethylethoxyforminium chloride.

The method (3) is carried out in the following way: A cephalosporin of the formula (VI) obtained in a known manner (Japanese Patent Application Kokai (Laid-Open) Nos. 70,788/76 and 113,890/76) is dissolved or suspended in an inert solvent such as, for example, tetrahydrofuran, dioxane, ethylene glycol dimethyl ether, methylene chloride, chloroform, dimethylformamide, dimethylacetamide, acetonitrile, methanol or the like or a mixture of two or more of these solvents. To the resulting solution or suspension is added an alkali metal methylate (VII) together with methanol. The resulting mixture is subjected to reaction, and the reaction mixture is then reacted with a halogenating agent. In this reaction, methanol is used in excess and the amount of the alkali metal methylate (VII) used is preferably 2 to 6 equivalents per equivalent of the cephalosporin (VI) used. The term "in excess" means an amount of more than one equivalent per equivalent of the cephalosporin (VI). All of the above reactions are carried out at −120° to −10° C., preferably −100° to −50° C. A reaction time of 5 to 30 minutes is sufficient and the reaction is terminated by acidifying the reaction system.

The halogenating agent used in this method is generally known to be a source for supplying a positive halogen atom such as Cl+, Br+ or I+. Examples of such halogenating agents include halogens such as chlorine, bromine and the like; N-haloimides such as N-chlorosuccinimide, N-bromosuccinimide and the like; N-haloamides such as N-chloroacetamide, N-bromoacetamide and the like; N-halosulfonamides such as N-chlorobenzenesulfonamide, N-chloro-p-toluenesulfonamide and the like; 1-halobenzotriazoles; 1-halotriazines; organic hypohalogenite such as tert.-butyl hypochlorite, tert.-butyl hypoiodide and the like; halohydantoins such as N,N-dibromohydantoin, and the like. Of these halogenating agents, tert.-butyl hypochlorite is preferred. The halogenating agent is used in an amount sufficient for supplying a positive halogen in an amount equivalent to that of the cephalosporin of the general formula (VI).

Suitable acids for the termination of reaction are those which, when added to a cold reaction mixture, will not cause solidification of the reaction mixture or freezing of the reaction mixture into a heavy viscous mixture. Examples of the suitable acids are 98% formic acid, glacial acetic acid, trichloroacetic acid and methanesulfonic acid.

After the termination of the reaction, the excess halogenating agent can be removed by treating with a reducing agent such as trialkyl phosphite, sodium thiosulfate, or the like.

In carrying out the production method (4), when a compound of the formula (VIII) is used other than the compound in which the group $R^7$ is a heterocyclic aromatic amine-N-oxide thio group having a thio group on the carbon atom adjacent to the N-oxide group, said compound is reacted with a compound of the formula (IX) in an inert solvent such as, for example, water, methanol, ethanol, propanol, isopropanol, butanol, acetone, methyl ethyl ketone, methyl isobutyl ketone, tetrahydrofuran, dioxane, acetonitrile, ethyl acetate, 2-methoxyethanol, dimethoxyethane, dimethylformamide, dimethyl sulfoxide, dimethylacetamide, dichloroethane, chloroform, dichloromethane, and the like, alone or in admixture of two or more.

The above reaction is carried out preferably in a strongly polar solvent such as water. It is advantageous to maintain the pH of the reaction solvent at 2 to 10, preferably 4 to 8. The reaction is effected after the addition of a buffer such as sodium phosphate to adjust the pH to a desired value. Although the reaction conditions are not critical, the reaction is generally carried out at 0° to 100° C. for several hours to several tens of hours.

When a compound of the general formula (VIII) in which the group $R^7$ is a heterocyclic aromatic amine-N-oxide thio group having a thio group on the carbon atom adjacent to the N-oxide group is used, the compound of the general formula (VIII) and a compound of the general formula (IX) are reacted with each other in the presence of a divalent copper compound. This procedure is particularly useful when the compound of the general formula (IX) is an alcohol such as methyl alcohol, ethyl alcohol, propyl alcohol, isopropyl alcohol, n-butyl alcohol, benzyl alcohol, ethylene glycol or the like. In this case, the reaction proceeds smoothly by the use of an excess of the alcohol to serve as a solvent. The divalent copper compounds used in this procedure are inorganic or organic divalent copper compounds such as, for example, cupric chloride, cupric bromide, cupric fluoride, cupric nitrate, cupric sulfate, cupric borate, cupric phosphate, cupric cyanide, cupric formate, cupric acetate, cupric propionate, cupric citrate, cupric tartrate, cupric benzoate, and cupric salicylate. The amount of the divalent copper compound used is preferably 0.5 mole or more per mole of the compound represented by the general formula (VIII). Although depending on the types of the compound of the general formula (VIII), divalent copper compound, and compound of the general formula (IX) used, generally the reaction temperature is 0° to 100° C., and the reaction time is several minutes to several days.

Conversion from a compound of the general formula (I) in which $R^1$ is a carboxyl-protecting group to a compound of the general formula (I) in which $R^1$ is a hydrogen atom or a salt of the latter compound, conversion from a compound of the general formula (I) in which $R^1$ is a hydrogen atom to a salt or to a compound of the general formula (I) in which $R^1$ is a carboxyl-protecting group, or conversion from a salt of a compound of the general formula (I) to its free acid can be carried out in a conventional manner.

In reacting a compound in which the group A, B or $R^2$ is reactive, the reactive group can be protected with a protecting group usually used in protecting a carboxyl, amino or hydroxyl group. After the reaction, such a protecting group can be removed in a conventional manner to regenerate the group A, B or $R^2$.

The conditions for the production are not limited to those described above, but suitably modified in accordance with the particular type of reagent used.

Isolation of a 7α-methoxycephalosporin (I) or a salt thereof from the reaction mixture can be carried out in a conventional manner.

The method for the production of a 7α-methoxycephalosporin represented by the general formula (I) and a salt thereof is not limited to those described above. These compounds can be produced also by other known methods.

The 7α-methoxycephalosporin represented by the general formula (I) and the salt thereof thus obtained are very useful for the therapy of man and mammals diseases because of their broad antibacterial spectrum against Gram-positive bacteria and Gram-negative bacteria, their excellent antibacterial activity to Gram-negative bacteria such as *Esherichiacoli, Klebsiella pneumoniae,* Protius species, *Serratia marcescens, Alkaligenes faecalis,* etc. and their stability to β-lactamase.

Among various 7α-methoxycephalosporins according to this invention, those represented by the following formula (Ia) and salts thereof are preferred:

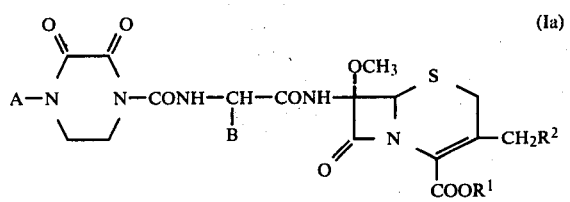

wherein A represents a hydrogen atom or a lower alkyl group; B represents a $C_{1-4}$alkyl group which is substituted by hydroxyl group; and $R^1$ and $R^2$ have the same meanings as defined above. Of the 7α-methoxycephalosporins represented by the above formula (Ia) and salts thereof, most preferred are those in which B is

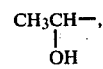

particularly those in which B is

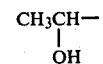

and $R^2$ is an acetoxy group, substituted 5-(1,2,3,4-tetrazolyl)thio group or 2-(1,3,4-thiadiazolyl)thio group.

Antibacterial activities of the representative compounds (Ib) of the 7α-methoxycephalosporins according to this invention are shown in Table 1.

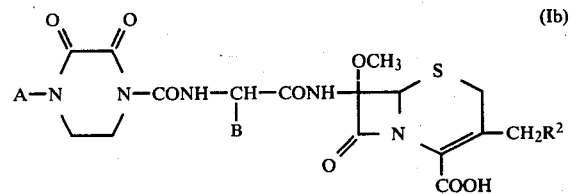

The figures given in Table 1 represent the minimum inhibitory concentration (MIC in mcg/ml) of each compound, which was determined according to the method described in "Chemotherapy (Society of Chemotherapy, Japan), Vol. 16, 98–99 (1968)": A culture obtained by cultivating the test bacterium in a Heart Infusion broth (Eiken Kagaku Co.) was inoculated into a Heart Infusion agar medium (Eiken Kagaku Co.). After 20 hours of the incubation at 37° C., the growth of the bacterium was inspected to determine the minimum inhibitory concentration (MIC in mcg/ml). The inoculation rate of the bacterium was $10^4$ cells/plate ($10^6$ cells/ml).

(1) Minimum inhibitory concentration (MIC in mcg/ml).

TABLE 1

| Bacteria | CS-1170 (control) | B: CH₃— R²: C₂H₅— | ClCH₂— C₂H₅— | (S) CH₃CH—OH C₂H₅— | (S) CH₃CH—OH CH₂CH₂OH | (S) CH₃CH—OH C₂H₅— (thiazoline) | (S) CH₃CH—OH C₂H₅— (—OCOCH₃) | (S) CH₃CH—OH n-C₄H₉— | HOCH₂— C₂H₅— | (R) CH₃CH—OH C₂H₅— | (S) CH₃CH—OCH₃ C₂H₅— | (S) CH₃CH—OCHO C₂H₅— |
|---|---|---|---|---|---|---|---|---|---|---|---|---|
| E. coli NIHJ | 0.39 | ≦0.1 | ≦0.1 | ≦0.1 | ≦0.1 | ≦0.1 | 0.2 | ≦0.1 | 0.2 | ≦0.1 | ≦0.1 | 0.2 |
| Kl. pneumoniae Y-50 | 0.39 | 0.39 | 0.2 | ≦0.1 | 0.2 | 0.2 | 0.2 | 0.2 | 0.39 | 0.2 | 0.2 | ≦0.1 |
| Ser. marcescens W-35 | 100 | 25 | 12.5 | 6.25 | 6.25 | 6.25 | 50 | 6.25 | 25 | 6.25 | 3.13 | 3.13 |
| Ser. marcescens IID620 | 3.13 | 0.78 | 0.39 | 0.2 | 0.2 | 0.2 | 1.56 | 0.39 | 1.56 | 0.78 | ≦0.1 | ≦0.1 |
| Pro. morganii T-216 | 12.5 | 6.25 | 6.25 | 1.56 | 3.13 | 3.13 | 12.5 | 3.13 | 12.5 | 3.13 | 0.39 | 1.56 |
| Aci. calcoaceticus A-6 | 50 | 50 | 50 | 12.5 | 50 | 50 | 50 | 25 | 50 | 12.5 | 12.5 | 50 |
| E. coli TK-3 (Penicillinase-producing bacterium) | 1.56 | 0.2 | 0.39 | ≦0.1 | 0.2 | 0.39 | 0.39 | ≦0.1 | 0.78 | 0.39 | ≦0.1 | ≦0.1 |
| Kl. pneumoniae Y-4 (Penicillinase-producing bacterium) | 1.56 | 1.56 | 1.56 | 0.39 | 0.39 | 0.78 | 0.78 | 0.78 | 0.78 | — | 0.78 | 0.39 |
| Klebsiella spp. Y-72 | 12.5 | 6.25 | 6.25 | 0.39 | 0.78 | 1.56 | 12.5 | 3.13 | 6.25 | 0.78 | 0.78 | 1.56 |
| Pro. vulgaris GN-76 (Cephalosporinase-producing bacterium) | 3.13 | 3.13 | 1.56 | 1.56 | 1.56 | 3.13 | 3.13 | 3.13 | 3.13 | 6.25 | 3.13 | 1.56 |
| Ser. marcescens W-8 (Cephalosporinase-producing bacterium) | >200 | 200 | 50 | 50 | 50 | 100 | 200 | 12.5 | 200 | 100 | 25 | 25 |
| Ent. cloacae IID977 | >200 | 200 | 100 | 50 | 50 | 100 | 200 | 50 | 50 | 50 | 25 | 25 |
| E. coli GN-5482 (Cephalosporinase-producing bacterium) | 50 | 25 | 12.5 | 6.25 | 6.25 | 12.5 | 12.5 | 3.13 | 25 | — | 6.25 | 6.25 |

Unit: mcg/ml

Note:

1. CS-1170 means NCCH₂SCH₂CONH—

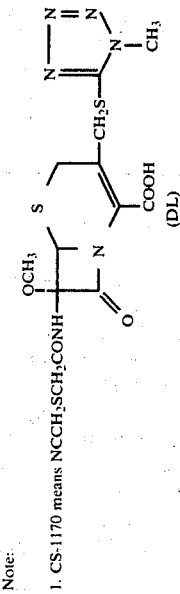

2. The compound (Ib) in which B is ClCH₂— is —CH— (DL), and the other compounds (Ib) are —CH— (D).

(2) Stability to β-lactamase.

The stability to β-lactamase was examined by iodometry at 30° C. by the method of Perret [Perret, C. J., "Iodometric assay of penicillinase", Nature, 174, 1012–1013 (1954)], except that a 0.1 M phosphate buffer solution (pH 7.0) was used in place of the 0.2 M phosphate buffer solution (pH 6.5). The stability of each compound was shown in Table 2 in terms of relative degree of hydrolysis, assuming the stability of Cephaloridin (CER) to cephalosporinase as 100 and the stability of Penicillin G (PC-G) to penicillinase as 100.

TABLE 2.

| Stability of β-lactamase | | | | | |
|---|---|---|---|---|---|
| Cephalosporinase- or penicillinase-producing bacteria | | PC-G | CER | CEZ | T-1982 |
| Cephalosporinase | E. coli GN-5482 | 22 | 100 | 130 | <0.1 |
|  | Ser. marcescens W-8 | 21 | 100 | 94 | 0.04 |
| Penicillinase | E. coli TK-3 | 100 | 115 | 21 | <0.12 |
|  | Kl. pneumoniae Y-4 | 100 | 41 | 4 | <0.55 |

Note:
CEZ means Cefazolin
T-1982 means

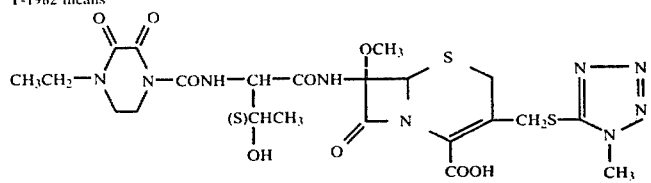

(3) Infection-protective activity.

Four-week old ICR-strain mice (male) in groups, each group consisting of five mice, were inoculated intraperitoneally with a prescribed quantity of a pathogenic bacterium suspended in 5% mucin. After one hour from the inoculation, the mice were subcutaneously administered with the test preparation to determine the infection-protective activity. The results obtained were as shown in Table 3. The figures in Table 3 represent the protective activity in terms of $ED_{50}$.

TABLE 3.

| | | Infection-protective activity | | | | |
|---|---|---|---|---|---|---|
| | | | MIC (mcg/ml) | | $ED_{50}$ (subcutaneous) (mg.mouse) | |
| Strain | Challenge dose (cells/mouse) | Inoculated bacteria quantity (cells/ml) | T-1982 | CS-1170 | T-1982 | CS-1170 |
| Pro. vulgaris GN-3027 | 8.0 × 10⁶ | 10⁸ | 0.78 | 1.56 | 0.067 | 0.82 |
|  |  | 10⁶ | 0.39 | 0.78 |  |  |
| Ser. marcescens IID 620 | 1.0 × 10⁷ | 10⁸ | <0.1 | 3.13 | 0.088 | 0.71 |
|  |  | 10⁶ | <0.1 | 0.78 |  |  |
| Kl. pneumoniae Y-50 | 1.9 × 10⁸ | 10⁸ | ≦0.1 | 0.78 | 0.10 | 0.73 |
|  |  | 10⁶ | ≦0.1 | 0.39 |  |  |

Note:
T-1982 is the same as defined in Table 2.
CS-1170 is the same as defined in Table 1.

The 7α-methoxycephalosporins of this invention are low-toxic. For instance, T-1982 showed a $LD_{50}$ of 5 g/kg or more (ICR-strain mice; intravenous).

The 7α-methoxycephalosporins of this invention represented by the general formula (I) and salts thereof are administered to man and mammals in the form of free acid or pharmaceutically acceptable salt or ester. The compound is formulated into various dosage forms which are customary in penicillin or cephalosporin preparations such as, for example, capsules, syrups and injections, and administered either orally or parenterally.

This invetion is illustrated below in detail with reference to Examples which, however, are merely illustrative and not limitative. In the Examples, all percentages are by weight unless otherwise indicated.

EXAMPLE 1

(1) To a suspension of 5.0 g of D(−)-alanine in 50 ml of methylene chloride was added 14.9 ml of trimethylchlorosilane. To the mixture was added dropwise 15.6 ml of triethylamine at 0° to 5° C. The temperature of the resulting mixture was gradually elevated and the reaction was allowed to proceed at 20° C. for 1.5 hrs. To the reaction mixture was then added at 5° to 10° C. 20 g of a mixture of 4-ethyl-2,3-dioxo-1-piperazinecarbonyl chloride and triethylamine hydrochloride, in which mixture, 58.02% was the former component. After reaction was effected at 20° C. for 2 hrs., the reaction mixture was freed from the solvent by distillation. To the residue was added 50 ml of water, and the pH of the mixture was adjusted to 7.5 with sodium hydrogen carbonate, after which the mixture was washed with 50 ml of ethyl acetate, and 50 ml of acetonitrile was added thereto. The pH thereof was adjusted to 1.5 with 2 N hydrochloric acid. The acetonitrile layer was separated and the aqueous layer was extracted twice with 50-ml portions of acetonitrile. The extract acetonitrile layers were washed with saturated aqueous sodium chloride solution and then combined with the above acetonitrile layer. The combined acetonitrile layer was dried over anhydrous magnesium sulfate and freed from the solvent by distillation under reduced pressure. The residue was recrystallized from n-butanol to obtain 10.8 g (yield 75%) of D(−)-α-(4-ethyl-2,3-dioxo-1-piperazinecarboxamido)propionic acid having a melting point of 164° to 168° C.

IR (KBr) cm$^{-1}$: $\nu_{C=O}$ 1710, 1660.

NMR (DMSO-d$_6$) δ values: 1.11 (3H, t, —CH$_3$), 1.39 (3H, d, —CH$_3$), 3.2–4.1 (6H, m, >CH$_2$×3), 4.3 (1H, m, >CH), 9.22 (1H, d, >NH)

(2) To a suspension of 1.5 g of D(−)-α-(4-ethyl-2,3-dioxo-1-piperazinecarboxamido)propionic acid in 15 ml of methylene chloride was added 0.64 ml of 1-methylmorpholine to form a solution. While maintaining the temperature at −15° to −20° C., 0.58 ml of ethyl chlorocarbonate was added to the solution and allowed to react for 1.5 hours. Thereafter, 2.88 g of diphenylmethyl 7β-amino-3-[5-(1-methyl-1,2,3,4-tetrazolyl)-thiomethyl]-Δ$^3$-cephem-4-carboxylate was added to the solution and the reaction was allowed to proceed for one hour at −15° to −20° C., and then for 1.5 hours at −10° to 0° C. After removing the solvent by distillation under reduced pressure, 30 ml of water and 30 ml of ethyl acetate were added to the residue and the mixture was stirred thoroughly. The precipitated white crystals were collected by filtration to obtain 4.0 g (yield 93.6%) of diphenylmethyl 7β-[D-(−)-α-(4-ethyl-2,3-dioxo-1-piperazinecarboxamido)-propionamido]-3-[5-(1-methyl-1,2,3,4-tetrazolyl)thiomethyl]-Δ$^3$-cephem-4-carboxylate having a melting point of 150° to 154° C. (decomp.).

IR (KBr) cm$^{-1}$: $\nu_{C=O}$ 1780, 1720, 1680.

NMR (CDCl$_3$) δ values: 1.08 (3H, t, —CH$_3$), 1.36 (3H, d, —CH$_3$), 3.25–4.0 (8H, m, >CH$_2$×4), 3.8 (3H, s, —CH$_3$), 4.3 (2H, q, >CH$_2$), 4.55 (1H, m, >CH), 4.99 (1H, d, >CH), 5.8 (1H, m, >CH), 6.85 (1H, s, >CH), 7.2–7.4 (10H, s, —C$_6$H$_5$×2), 7.7 (1H, s, >CH), 9.3 (1H, s, >NH).

(3) In a mixture of 20 ml of chloroform and 6 ml of anhydrous tetrahydrofuran was dissolved 1.26 g of diphenylmethyl 7β-[D(−)-α-(4-ethyl-2,3-dioxo-1-piperazinecarboxamido)-propionamido]-3-[5-(1-methyl-1,2,3,4-tetrazolyl)thiomethyl]-Δ$^3$-cephem-4-carboxylate. While maintaining the temperature at −70° C., 2.75 ml of a solution of lithium methoxide (2.184 mM/ml) in methanol was added thereto. The resulting solution was stirred for 3 minutes, and 0.31 ml of tert.-butyl hypochlorite was added and the solution was stirred for 15 minutes at the same temperature. After addition of 0.4 ml of acetic acid, the temperature of the reaction system was elevated to room temperature. The reaction mixture was poured into 30 ml of a citrate buffer solution (pH 7.0). The organic layer was separated, washed with water, and then dried over magnesium sulfate, and thereafter freed from the solvent by distillation under reduced pressure. The residue was purified by a column chromatography (stationary phase: silica gel; eluent: a 1:3 mixture of benzene and ethyl acetate) to obtain 0.6 g (yield 45.8%) of diphenylmethyl 7β-[D(−)-α-(4-ethyl-2,3-dioxo-1-piperazinecarboxamido)-propionamido]-7α-methoxy-3[5-(1-methyl-1,2,3,4-tetrazolyl)thiomethyl]-Δ$^3$-cephem-4-carboxylate.

IR (KBr) cm$^{-1}$: $\nu_{C=O}$ 1770, 1700, 1670.

NMR (CDCl$_3$) δ values: 1.1 (3H, t, —CH$_3$), 1.5 (3H, d, —CH$_3$), 3.5 (3H, s, —CH$_3$), 3.3–4.2 (8H, m, >CH$_2$×4), 3.8 (3H, s, —CH$_3$), 4.35 (2H, q, >CH$_2$), 4.6 (1H, m, >CH), 5.03 (1H, s, >CH), 6.88 (1H, s, >CH), 7.2–7.4 (10H, s, —C$_6$H$_5$×2), 8.0 (1H, s, >NH), 9.25 (1H, d, >NH).

(4) In 8 ml of anisole was dissolved 1.2 g of diphenylmethyl 7β-[D(−)-α-(4-ethyl-2,3-dioxo-1-piperazinecarboxamido)-propionamido]-7α-methoxy-3-[5-(1-methyl-1,2,3,4-tetrazolyl)thiomethyl]-Δ$^3$-cephem-4-carboxylate, and 5 ml of trifluoroacetic acid was added to the solution with ice-cooling. The solution was stirred at the same temperature for 30 minutes. After completion of the reaction, the solvent was removed by distillation under reduced pressure. The residue was dissolved by adding 30 ml of ethyl acetate and 30 ml of water and the pH of the solution was adjusted to 7.0 with aqueous sodium hydrogen carbonate solution. The aqueous layer was separated, and 30 ml of acetonitrile was added thereto, after which the pH thereof was adjusted to 2.0 with 2 N hydrochloric acid. The acetonitrile layer was separated and the aqueous layer was extracted twice with 30-ml portions of acetonitrile. The extract acetonitrile layers were washed with saturated aqueous sodium chloride solution and then combined with the above acetonitrile layer. The combined acetonitrile layer was dried over anhydrous magnesium sulfate and freed from the solvent by distillation under reduced pressure to obtain 0.5 g (yield 53.2%) of 7β-[D(−)-α-(4-ethyl-2,3-dioxo-1-piperazinecarboxamido)-propionamido]-7α-methoxy-3[5-(1-methyl-b 1,2,3,4-tetrazolyl)-thiomethyl]-Δ$^3$-cephem-4-carboxylic acid having a melting point of 165° C. (decomp.).

IR (KBr) cm$^{-1}$: $\nu_{C=O}$ 1770, 1705, 1670, 1650.

NMR (DMSO-d$_6$) δ values: 1.12 (3H, t, —CH$_3$), 1.40 (3H, d, —CH$_3$), 3.44 (3H, s, —CH$_3$), 3.4–4.2 (8H, m, >CH$_2$×4), 3.99 (3H, s, —CH$_3$), 4.3 (2H, q, >CH$_2$), 4.5 (1H, m, >CH), 5.1 (1H, s, >CH), 9.13 (1H, d, >NH), 9.40 (1H, s, >NH).

In a similar manner, the following compounds were obtained:

7β-[DL-α-(4-ethyl-2,3-dioxo-1-piperazinecarboxamido)-α-(chloromethyl)-acetamido]-7α-methoxy-3-[5-(1-methyl-1,2,3,4-tetrazolyl)thiomethyl]-Δ$^3$-cephem-4-carboxylic acid, m.p. 143°–146° (decomp.).

IR (KBr) cm$^{-1}$: $\nu_{C=O}$ 1775, 1730–1650.

NMR (DMSO-d$_6$) δ values: 1.15 (3H, t, —CH$_3$), 3.45 (3H, s, —OCH$_3$), 3.97 (3H, s, —CH$_3$), 3.30–4.10 (10H, m, >CH$_2$×5), 4.30 (2H, bs, >CH$_2$), 4.95 (1H, m, >CH), 5.05 (1H, s, >CH), 9.45 (1H, d, >NH), 9.60 (1H, s, >NH).

7β-[DL-α-(4-ethyl-2,3-dioxo-1-piperazinecarboxamido)-α-(hydroxymethyl)-acetamido)-7α-methoxy-3-[5-(1-methyl-1,2,3,4-tetrazolyl)thiomethyl]-Δ$^3$-cephem-4-carboxylic acid, m.p. 108°–110° C. (decomp.).

IR (KBr) cm$^{-1}$: $\nu_{C=O}$ 1765, 1720–1650.

7β-[DL-α-(2,3-dioxo-1-piperazinecarboxamido)-propionamido]-7α-methoxy-3-[5-(1-methyl-1,2,3,4-tetrazolyl)thiomethyl]-Δ$^3$-cephem-4-carboxylic acid.

EXAMPLE 2

(1) In 50 ml of methylene chloride was suspended 2.0 g of D-threonine, and 6.58 ml of trimethylchlorosilane was added to the resulting suspension, after which 7.01 ml of triethylamine was added dropwise thereto at 0° to 5° C. The temperature of the suspension was gradually elevated, and reaction was effected at 20° C. for 1.5 hrs., after which 5.9 g of a mixture of 4-ethyl-2,3-dioxo-1-piperazinecarbonyl chloride and triethylamine hydrochloride (the content of 4ethyl-2,3-dioxo-1-piperazinecarbonyl chloride was 58.55% by weight) was added to the reaction mixture. The resulting mixture was subjected to reaction at 20° C. for 1 hr and then distilled under reduced pressure to remove the solvent. To the residue was added 30 ml of water, and the pH of the resulting solution was adjusted to 7.5 with sodium hydrogen carbonate, after which the solution was washed with 50 ml of ethyl acetate and then 50 ml of acetonitrile was added to the solution. The pH of the resulting mixture was adjusted to 1.5 with 2 N hydrochloric acid. Sodium chloride was added to the mixture to saturate the same, and the acetonitrile layer was thereafter separated.

The aqueous layer was subjected to extraction with four 50-ml portions of acetonitrile, and the four extract acetonitrile layers were combined with the above-mentioned acetonitrile layer, and the combined acetonitrile layer was washed with saturated sodium chloride solution, after which the acetonitrile layer was dried over anhydrous magnesium sulfate, and then distilled under reduced pressure to remove the solvent. The residue was recrystallized from n-butanol to obtain 3.6 g (yield 75%) of D-α-(4-ethyl-2,3-dioxo-1-piperazinecarboxamido)-β-(S)-hydroxybutyric acid having a melting point of 164° to 166° C.

IR (KBr) cm$^{-1}$: $\nu_{C=O}$ 1740, 1710, 1670.

NMR (DMSO-d$_6$) δ values: 1.11 (3H, t, —CH$_3$), 1.13 (3H, d, —CH$_3$), 3.28–3.75 (4H, m, >CH$_2$×2), 3.78–4.30 (4H, m, >CH$_2$, >CH×2).

(2) In 15 ml of methylene chloride was suspended 1.0 g of D-α-(4-ethyl-2,3-dioxo-1-piperazinecarboxamido)-β-(S)-hydroxybutyric acid, and 0.38 ml of 1-methylmorpholine was added thereto to convert the suspension to a solution. To the solution was added 0.35 ml of ethyl chlorocarbonate at −15° to −20° C., and the solution was subjected to reaction at the same temperature for 1.5 hrs. Thereafter, 1.67 g of diphenylmethyl 7β-amino-3-[5-(1-methyl-1,2,3,4-tetrazolyl)thiomethyl]-Δ$^3$-cephem-4-carboxylate was added to the reaction mixture, and the resulting mixture was subjected to reaction at the same temperature for 1hr, and then at −10° to 0° C. for 1.5 hrs. The reaction mixture was distilled under reduced pressure to remove the solvent, and to the residue were added 30 ml of water and 30 ml of ethyl acetate, after which the resulting solution was stirred. The thus precipitated white crystals were collected by filtration to obtain 2.5 g (yield 95%) of diphenylmethyl 7β-[D-α-(4-ethyl-2,3-dioxo-1-piperazinecarboxamido)-β-(S)-hydroxybutanamido]-3-[5-(1-methyl-1,2,3,4-tetrazolyl)thiomethyl]-Δ$^3$-cephem-4-carboxylate having a melting point of 121° to 125° C. (decomp.).

IR (KBr) cm$^{-1}$: $\nu_{C=O}$ 1785, 1720, 1680.

NMR (DMSO-d$_6$) δ values: 1.00 (3H, t, —CH$_3$), 1.16 (3H, d, —CH$_3$), 3.4–4.0 (10H, m, >CH$_2$×4, >CH×2), 3.85 (3H, s, —CH$_3$), 4.25 (2H, q, >CH$_2$), 5.10 (1H, d, >CH), 5.8 (1H, m, >CH), 6.85 (1H, s, >CH), 7.2–7.45 (10H, s, —C$_6$H$_5$×2), 8.91 (1H, s, >NH), 9.26 (1H, s, >NH).

(3) In a mixture of 30 ml of dried methylene chloride and 2 ml of dried tetrahydrofuran was dissolved 1.0 g of diphenylmethyl 7β-[D-α-(4-ethyl-2,3-dioxo-1-piperazinecarboxamido)-β-(S)-hydroxybutanamido]-3-[5-(1-methyl-1,2,3,4-tetrazolyl)thiomethyl]-Δ$^3$-cephem-4-carboxylate, and the resulting solution was cooled to −70° C. To the cooled solution was added 3.55 ml (1.66 mM/ml) of a methanol solution of lithium methoxide at the same temperature, and the resulting mixture was stirred for 3 min, after which 0.18 ml of tert.-butyl hypochlorite was added thereto. The resulting mixture was stirred at the same temperature for 15 min, after which 0.39 ml of acetic acid was added to the resulting solution, and the temperature of the solution was elevated to room temperature. The solution was distilled under reduced pressure to remove the solvent, and to the residue were added 20 ml of ethyl acetate and 20 ml of water to dissolve the residue, after which the pH of the resulting solution was adjusted to 6.5 with aqueous sodium bicarbonate solution. The organic layer was separated, washed with water, then dried over anhydrous magnesium sulfate, and thereafter distilled under reduced pressure to remove the solvent. The residue was purified by a column chromatography [Wako silica gel C-200; eluted with a mixture of benzene and ethyl acetate (1:2 by volume)], upon which 0.6 g (yield 40.8%) of diphenylmethyl 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ$^3$-cephem-4-carboxylate.

IR (KBr) cm$^{-1}$: $\nu_{C=O}$ 1780, 1710, 1670.

NMR (CDCl$_3$) δ values: 1.20 (3H, t, —CH$_3$), 1.25 (3H, d, —CH$_3$), 3.5 (3H, s, —CH$_3$), 3.79 (3H, s, —CH$_3$), 3.2–4.0 (8H, m, >CH$_2$×4), 4.3–4.6 (4H, m, >CH$_2$, >CH×2), 5.02 (1H, s, >CH), 6.85 (1H, s, >NH), 7.2–7.4 (10H, s, —C$_6$H$_5$×2), 8.52 (1H, s, >NH), 9.55 (1H, d, >NH).

(4) In 5 ml of anisole was dissolved 0.5 g of diphenylmethyl 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ4-carboxylate, and 5 ml of trifluoroacetic acid was added to the resulting solution with ice-cooling, after which the resulting solution was stirred at the same temperature for 30 min. The reaction mixture was distilled under reduced pressure to remove the solvent, and to the residue were added 10 ml of ethyl acetate and 10 ml of water, after which saturated sodium hydrogen carbonate solution was added thereto with stirring to adjust the pH thereof to 6.5, thereby dissolving the residue. The aqueous layer was separated, to which 10 ml of methyl acetate was then added. The pH of the resulting mixture was adjusted to 2.0 with 2 N hydrochloric acid. The organic layer was separated. The aqueous layer was extracted with two 10-ml portions of methyl acetate, and the two extracts were combined with the above-mentioned organic layer, and the combined organic layer was washed with saturated aqueous sodium chloride solution.

After drying over anhydrous magnesium sulfate, the organic layer was distilled under reduced pressure to remove the solvent, and the residue was treated with diethyl ether to obtain 0.25 g (yield 63.3%) of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ$^3$- cephem-4-carboxylic acid having a melting point of 118° to 120° C. (decomp.).

IR (KBr) cm$^{-1}$; $\nu_{C=O}$ 1770, 1705, 1675.

NMR (DMSO-d$_6$) δ values: 1.10 (3H, t, —CH$_3$), 1.15 (3H, d, —CH$_3$), 3.40 (3H, s, —CH$_3$), 3.93 (3H, s, —CH$_3$), 3.5–4.0 (8H, m, >CH$_2$×4), 4.1–4.4 (4H, m, >CH$_2$, >CH×2), 5.03 (1H, s, >CH), 9.2 (2H, d, >NH×2).

In the same manner as above, the following compounds were obtained:

7β-[D-α-(4-ethyl-2,3-dioxo-1-piperazinecarboxamido)-β-hydroxypropionamido]-7α-methoxy-3-[5-(1-methyl-1,2,3,4-tetrazolyl)thiomethyl]-Δ$^3$-cephem-4-carboxylic acid, m.p. 125° to 130° C. (decomp.).

IR (KBr) cm$^{-1}$: $\nu_{C=O}$ 1780, 1720, 1710, 1670.

NMR (DMSO-d$_6$) δ values: 1.15 (3H, t, —CH$_3$), 3.30–4.10 (10H, m, >CH$_2$×5), 3.45 (3H, s, —CH$_3$), 3.95 (3H, s, —CH$_3$), 4.33 (2H, ABq, >CH$_2$), 4.50 (1H, m, >CH), 5.05 (1H, s, >CH), 9.30 (2H, bs, >NH×2).

7β-[D-α-(4-ethyl-2,3-dioxo-1-piperazinecarboxamido)-β-(S)-hydroxybutanamido]-7α-methoxy-3-[2-(1,3,4-thiadiazolyl)thiomethyl]-Δ$^3$-cephem-4-carboxylic acid, m.p. 108° to 112° C. (decomp.).

IR (KBr) cm$^{-1}$: $\nu_{C=O}$ 1780, 1720, 1680.

NMR (DMSO-d$_6$+D$_2$O) δ values: 1.02–1.39 (6H, m, —CH$_3$×2), 3.50 (3H, s, —CH$_3$), 3.3–4.5 (12H, m, >CH$_2$×5, >CH×2), 5.05 (1H, s, >CH), 9.42 (1H, s, >CH).

7β-[D-α-(4-n-octyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ$^3$-cephem-4-carboxylic acid, m.p. 113° to 115° C. (decomp.).

IR (KBr) cm$^{-1}$: $\nu_{C=O}$ 1780, 1660–1720.

NMR (CD$_3$COCD$_3$) δ values: 0.80–1.60 (18H, m, >CH$_2$×6, —CH$_3$×2), 3.30–4.50 (12H, m, >CH$_2$×5, >CH×2), 3.48 (3H, s, —CH$_3$), 3.95 (3H, s, —CH$_3$), 5.00 (1H, s, >CH), 8.37 (1H, s, >NH), 9.40 (1H, d, >NH).

7β-[D-α-(4-n-butyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ$^3$-cephem-4-carboxylic acid, m.p. 125°–133° C. (decomp.).

IR (KBr) cm$^{-1}$: $\nu_{C=O}$ 1785, 1710, 1680.

NMR (DMSO-d$_6$) δ values: 0.80–1.60 (10H, m, >CH$_2$×2, —CH$_3$×2), 3.20–4.40 (12H, m, >CH$_2$×5, >CH×2), 3.41 (3H, s, —CH$_3$), 3.94 (3H, s, —CH$_3$), 5.08 (1H, s, >CH), 9.27 (1H, s, >NH), 9.30 (1H, d, >NH).

7β-[D-α-(4-ethyl-2,3-dioxo-1-piperazinecarboxamido)-β-(R)-hydroxybutanamido]-7α-methoxy-3-[5-(1-methyl-1,2,3,4-tetrazolyl)thiomethyl]-Δ$^3$-cephem-4-carboxylic acid, m.p. 144° to 150° C. (decomp.).

IR (KBr) cm$^{-1}$: $\nu_{C=O}$ 1780, 1735–1660.

NMR (CD$_3$COCD$_3$: DMSO-d$_6$=4:1 by volume) δ values: 0.96–1.37 (6H, m, —CH$_3$×2), 3.30–4.92 (12H, m, >CH$_2$×5, >CH×2), 3.54 (3H, s, —CH$_3$), 4.04 (3H, s, —CH$_3$), 5.10 (1H, s, >CH), 9.23 (1H, bs, >NH), 9.46 (1H, d, >NH).

EXAMPLE 3

(1) In 45 ml of methylene chloride was suspended 4.5 g of D-α-(4-ethyl-2,3-dioxo-1-piperazinecarboxamido)-β-(S)-hydroxybutyric acid, and 1.60 g of N-methylmorpholine was added to the resulting suspension to convert the suspension to a solution. The solution was cooled to −20° C., and 1.78 g of ethyl chlorocarbonate was added thereto, after which the resulting solution was subjected to reaction at −13° to −16° C. for 1.5 hrs. Subsequently, 6.50 g of diphenylmethyl 7β-amino-3-acetoxymethyl-Δ$^3$-cephem-4-carboxylate was added to the reaction mixture at −30° C. Reaction was effected at −10° to −15° C. for 30 min and then at −10° to 0° C. for 30 min, after which the reaction mixture was distilled under reduced pressure to remove the solvent. To the residue were added 50 ml of ethyl acetate, 50 ml of methyl acetate and 40 ml of water to dissolve the residue. The organic layer was separated, dried over anhydrous magnesium sulfate, and thereafter distilled under reduced pressure to remove the solvent. The residue was purified by a column chromatography [Wako silica gel C-200; eluted with a mixture of chloroform and ethanol (60:1 by volume)] to obtain 8.2 g (yield 78.2%) of white powder of diphenylmethyl 7β-[D-α-(4-ethyl-2,3-dioxo-1-piperazinecarboxamido-β-(S)-hydroxybutanamido]-3-acetoxymethyl-Δ$^3$-cephem-4-carboxylate.

IR (KBr) cm$^{-1}$: $\nu_{C=O}$ 1780, 1705, 1670.

(2) In 80 ml of methylene chloride was dissolved 8.0 g of the diphenylmethyl 7β-[D-α-(4-ethyl-2,3-dioxo-1-piperazinecarboxamido)-β-(S)-hydroxybutanamido]-3-acetoxymethyl-Δ$^3$-cephem-4-carboxylate obtained in above (1), and to the solution was added 26 ml of a methanol solution of lithium methoxide (the lithium methoxide content, 1.51 mM/ml) at −70° C. The solution was stirred at −65° to −70° C. for 3 min, and 1.60 g of tert.-butyl hypochlorite was thereafter added to the solution, after which reaction was effected at the same temperature for 15 min. To the reaction mixture was added 3 ml of acetic acid, and the temperature of the mixture was gradually elevated to 0° C., after which the mixture was distilled under reduced pressure to remove the solvent. To the residue were added 100 ml of ethyl acetate and 50 ml of water to dissolve the residue, and the organic layer was separated, dried over anhydrous magnesium sulfate and then distilled under reduced pressure to remove the solvent. The residue was purified by a column chromatography (Wako silica gel C-200; eluted with ethyl acetate) to obtain 2.65 g (yield 31.8%) of white powder of diphenylmethyl 7β-[D-α-(4-ethyl-2,3-dioxo-1-piperazinecarboxamido)-β-(S)-hydroxybutanamido]-7α-methoxy-3-acetoxymethyl-Δ$^3$-cephem-4-carboxylate.

IR (KBr) cm$^{-1}$: $\nu_{C=O}$ 1780, 1740, 1710, 1680.

(3) To 2.65 g of the diphenylmethyl 7β-[D-α-(4-ethyl-2,3-dioxo-1-piperazinecarboxamido)-β-(S)-hydroxybutanamido]7α-methoxy-3-acetoxymethyl-Δ$^3$-cephem-4-carboxylate obtained in above (2) were added 26 ml of anisole and 26 ml of trifluoroacetic acid with ice-cooling, and the resulting mixture was subjected to reaction at the same temperature for 30 min, after which the reaction mixture was distilled under reduced pressure to remove the solvent. Diethyl ether was added to the residue to wash the latter, thereby obtaining 2.0 g (yield 97.6%) of white powder of 7β-[D-α-(4-ethyl-2,3-dioxo-1-piperazinecarboxamido)-β-(S)-hydroxybutanamido]-7α-methoxy-3-acetoxymethyl-Δ$^3$-cephem-4-carboxylic acid having a melting point of 142° to 145° C. (decomp.).

IR (KBr) cm$^{-1}$: $\nu_{C=O}$ 1780, 1705, 1670.

NMR (CD$_3$COCD$_3$ : DMSO-d$_6$=4:1 by volume) δ values: 0.85–1.45 (6H, m, —CH$_3$×2), 2.03 (3H, s, —CH$_3$), 3.15–4.95 (12H, m, >CH$_2$×5, >CH×2), 3.48 (3H, s, —CH$_3$), 5.06 (1H, s, >CH), 8.84 (1H, s, >NH), 9.34 (1H, d, >NH).

EXAMPLE 4

In 24 ml of nitromethane were dissolved 0.71 g of 7β-[D-α-(4-ethyl-2,3-dioxo-1-piperazinecarboxamido)-β-(S)-hydroxybutanamido]-7α-methoxy-3-acetoxymethyl-Δ$^3$-cephem-4-carboxylic acid and 0.22 g of 1-(2-hydroxyethyl)-5-mercapto-1H-tetrazole, and the resulting solution was subjected to reaction at 80° C. for 5 hrs, after which the reaction mixture was distilled under reduced pressure to remove the solvent. To the resulting residue were added 20 ml of ethyl acetate and 20 ml of acetone to dissolve the residue. To the resulting solution was then added diphenyldiazomethane until the redish violet color remained without vanishing, and the resulting mixture was thereafter distilled under reduced pressure to remove the solvent. The resulting residue was purified by a column chromatography [Wako silica gel C-200; eluted with a mixture of chloroform and ethanol (20:1 by volume)] to obtain a pale yellow powder. To the powder were added 3.5 ml of anisole and 3.5 ml of trifluoroacetic acid with ice-cooling, and the resulting mixture was subjected to reaction at the same temperature for 30 min, after which the reaction mixture was distilled under reduced pressure to remove the solvent. Ethyl acetate was added to the resulting residue to wash the latter, upon which there was obtained 0.28 g (yield 34%) of a pale yellow powder of 7β-[D-α-(4-ethyl-2,3-dioxo-1-piperazinecarboxamido)-β-(S)-hydroxybutanamido]-7α-methoxy-3-{5-[1-(2-hydroxyethyl)-1,2,3,4-tetrazolyl]thiomethyl}-Δ³-cephem-4-carboxylic acid having a melting point of 128° to 135° C. (decomp.).

IR (KBr) cm$^{-1}$: $\nu_{C=O}$ 1780, 1710, 1675.

NMR (CD$_3$COCD$_3$ : DMSO-d$_6$=4:1 by volume) δ values: 0.9–1.4 (6H, m, —CH$_3$×2), 3.47 (3H, s, —CH$_3$), 3.20–4.60 (16H, m, >CH$_2$×7, >CH×2), 5.03 (1H, s, >CH), 9.01 (1H, s, >NH), 9.31 (1H, d, >NH).

EXAMPLE 5

In 7 ml of anhydrous methylene chloride was dissolved 0.20 g of D-α-(4-ethyl-2,3-dioxo-1-piperazinecarboxamido)-β-(S)-tert.-butoxybutyric acid, after which 0.10 g of oxalyl chloride and one drop of dimethylformamide were added to the resulting solution in this order with ice-cooling, and the resulting mixture was subjected to reaction at room temperature for 30 min. The reaction mixture was distilled under reduced pressure to remove the solvent. The resulting residue was dissolved in 8 ml of anhydrous methylene chloride, and the resulting solution was cooled to −50° C. To the solution were added 0.3 g of diphenylmethyl 7β-amino-7α-methoxy-3-[5-(1-methyl-1,2,3,4-tetrazolyl)thiomethyl]-Δ³-cephem-4-carboxylate and 0.1 ml of dimethylaniline in this order, after which the resulting mixture was subjected to reaction at −20° C. overnight. The reaction mixture was distilled under reduced pressure to remove the solvent, and the resulting residue was dissolved in a mixture of 10 ml of water and 15 ml of ethyl acetate, after which the ethyl acetate layer was separated, washed thoroughly with water, and then distilled to remove the solvent. The resulting residue was purified by a column chromatography [Wako silica gel C-200; eluted with a mixture of benzene and ethyl acetate (2:1 by volume)] to obtain 0.31 g (yield 63%) of diphenylmethyl 7β-[D-α-(4-ethyl-2,3-dioxo-1-piperazinecarboxamido)-β-(S)-tert.-butoxybutanamido]-7α-methoxy-3-[5-(1-methyl-1,2,3,4-tetrazolyl)thio-methyl]-Δ³-cephem-4-carboxylate having a metling point of 109° to 115° C. (decomp.).

IR (KBr) cm$^{-1}$: $\nu_{C=O}$ 1780, 1720–1680.

NMR (CDCl$_3$) δ values: 1.30 (9H, s, —CH$_3$×3), 1.03–1.55 (6H, m, —CH$_3$×2), 3.51 (3H, s, —CH$_3$), 3.72 (3H, s, —CH$_3$), 3.18–4.68 (12H, m, >CH$_2$×5, >CH×2), 4.98 (1H, s, >CH), 6.76 (1H, s, >CH) 7.22 (10H, bs, —C$_6$H$_5$×2), 8.04 (1H, bs, >NH), 9.50 (1H, d, >NH).

The above product was dissolved in a mixture of 2 ml of anisole and 2 ml of trifluoroacetic acid, and the resulting solution was subjected to reaction at room temperature for 30 min. The reaction mixture was dried under reduced pressure to dryness, after which 10 ml of ethyl acetate was added to the residue, and the resulting mixture was stirred for one hour. The crystals thus precipitated were collected by filtration and dried to obtain 0.21 g (yield 55.7%) of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid. The melting point (decomp.), IR spectrum and NMR spectrum of this product were identical with those of the product obtained in Example 2.

EXAMPLE 6

In a mixture of 40 ml of anhydrous methylene chloride and 20 ml of anhydrous methanol was dissolved 1 g of 7β-[D-α-(4-ethyl-2,3-dioxo-1-piperazinecarboxamido)-β-(S)-hydroxybutanamido]-3-[5-(1-methyl-1,2,3,4-tetrazolyl)thiomethyl]-Δ³-cephem-4-carboxylic acid, and the resulting solution was cooled to −75° C. To the solution was added dropwise 3.7 ml of lithium methoxide solution in methanol (9.2 mM lithium methoxide was contained therein), and the solution was subjected to reaction at −75° to −70° C. for 3 min, after which 0.22 ml of tert.-butyl hypochlorite was added thereto, and the resulting mixture was subjected to reaction for 15 min. To the reaction mixture was added 0.28 ml of formic acid, and the temperature of the mixture was elevated to room temperature. The mixture was distilled under reduced pressure to remove the solvent, and 4 ml of water, 4 ml of saturated aqueous sodium chloride solution and 20 ml of acetonitrile were added to the resulting residue to dissolve the residue. To the resulting solution was added dropwise 6 N hydrochloric acid to adjust the pH of the solution to 1.2. The organic layer was separated and then dried over anhydrous magnesium sulfate, and then distilled under reduced pressure to remove the solvent. To the resulting residue was added 14 of acetone and the resulting mixture was stirred. The crystals thus precipitated were collected by filtration, to obtain 0.71 g of the acetone adduct of 7β-[D-α-(4-methyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cepham-4-carboxylic acid.

The said adduct was suspended in 4.3 ml of 20% hydrous acetone, and sodium hydrogen carbonate was added to the suspension to adjust the pH thereof to 5.0. To the suspension was added 70 mg of active carbon, and the mixture was stirred for 3 to 4 min, and then filtered through celite to remove the active carbon. The pH of the filtrate was adjusted to 1.5 with 6 N hydrochloric acid. The filtrate was then stirred at room temperature for 30 min and then with ice-cooling for 3 hrs, after which the crystals thus precipitated were collected by filtration and then dried to obtain 0.5 g (yield 45%) of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid dihydrate having a melting point of 173° to 175° C. (decomp.).

IR (KBr) cm$^{-1}$: $\nu_{C=O}$ 1775, 1710, 1657, 1660.

The NMR spectrum of the product was identical with that of the product in Example 2.

EXAMPLE 7

In 20 ml of anhydrous methylene chloride was suspended 1 g of 7β-[D-α-(4-ethyl-2,3-dioxo-1-piperazinecarboxamido)-β-(S)-hydroxybutanamido]-3-[5-(1-methyl-1,2,3,4-tetrazolyl)thiomethyl]-Δ³-cephem-4-carboxylic acid, and to the suspension were added 0.8 ml of vinyl ethyl ether and 42 mg of pyridinium p-toluenesulfonate, and the resulting mixture was subjected to reaction under reflux for 50 min to produce 7β-{D-α-(4-ethyl-2,3-dioxo-1-piperazinecarboxamido)-β-(S)-[1-(1-ethoxyethyl)oxy]-butanamido}-3-[5-(1-methyl-1,2,3,4-tetrazolyl)-thiomethyl]-Δ³-cepham-4-carboxylic acid. The reaction mixture was cooled to −75° C., and 0.5 ml of anhydrous methanol was added thereto, after which 2.87 ml of lithium methoxide solution in methanol (7.52 mM of lithium methoxide was contained therein) was dropped thereinto. The resulting mixture was subjected to reaction at −75° to −70° C. for 3 min, after which 3 ml of anhydrous methylene chloride containing 0.25 ml of tert.-butyl hypochlorite was added dropwise thereto over 10 min. The resulting mixture was subjected to reaction at the same temperature for a further 5 min, after which 0.34 ml of acetic acid was added thereto, and the temperature of the resulting mixture was elevated to 0° C. To the reaction mixture was added 5 ml of water, and the resulting mixture was stirred, after which the organic layer was separated and distilled under reduced pressure to remove the solvent. The resulting residue (7β-{D-α-(4-ethyl-2,3-dioxo-1-piperazinecarboxamido)-β-(S)-[1-(1-ethoxyethyl)-oxy]-butanamido}-7α-methoxy-3-[5-(1-methyl-1,2,3,4-tetrazolyl)thiomethyl]-Δ³-cepham-4-carboxylic acid was contained therein) was dissolved in 15 ml of acetone, and 30 mg of p-toluenesulfonic acid monohydrate was added to the solution, and the solution was stirred at room temperature for 2 hrs and then allowed to stand at 5° C. overnight. The crystals thus precipitated were collected by filtration and then washed with water to obtain 0.85 g of the acetone adduct of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cepham-4-carboxylic acid.

This adduct was suspended in 5 ml of 20% hydrous acetone, and the pH thereof was adjusted to 5.0 by adding thereto sodium hydrogen carbonate, after which 85 mg of active carbon was added thereto, and the resulting mixture was stirred for 3 to 4 min, and then filtered through celite to remove the active carbon. To the filtrate was added 6 N hydrochloric acid to adjust the pH of the filtrate to 1.5, after which the filtrate was stirred at room temperature for 30 min and then with ice-cooling for 3 hrs. The crystals thus precipitated were collected by filtration to obtain 0.66 g (yield 60%) of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid dihydrate having a melting point of 173° to 175° C. (decomp.).

The IR spectrum and NMR spectrum of this product were identical with those of the product in Example 6.

EXAMPLE 8

(1) In 50 ml of anhydrous methylene chloride was dissolved 2.5 g of diphenylmethyl D-α-(4-ethyl-2,3-dioxo-1-piperazinecarboxamido)-β-(S)-hydroxybutyrate, and to the solution was added at −40° C. boron trifluoride-diethyl ether complex ($BF_3$ content: 47% by weight) and 50 ml of diethyl ether solution of diazomethane (the diazomethane content: about 1.4 g) in this order. The mixture was subjected to reaction. The temperature of the reaction mixture was thereafter elevated gradually to room temperature, and 20 ml of water was added to the mixture, after which the organic layer was separated, washed with saturated aqueous sodium chloride solution, dried over anhydrous magnesium sulfate, and then distilled under reduced pressure to remove the solvent. The resulting residue was purified by a column chromatography [Wako silica gel C-200; eluted with a mixture of benzene and ethyl acetate (5:1 by volume)] to obtain 0.68 g (yield 26.4%) of diphenylmethyl D-α-(4-ethyl-2,3-dioxo-1-piperazinecarboxamido)-α-(S)-methoxybutyrate.

(2) In a mixture of 5 ml of anisole and 5 ml of trifluoroacetic acid was dissolved 0.6 g of the diphenylmethyl D-α-(4-ethyl-2,3-dioxo-1-piperazinecarboxamido)-β-(S)-methoxybutyrate obtained in above (1), and the resulting solution was subjected to reaction with ice-cooling for 30 min. The reaction mixture was distilled under reduced pressure to remove the solvent, and to the residue were added 10 ml of diethyl ether and 10 ml of diisopropyl ether, and the resulting mixture was stirred for one hour. The crystals thus precipitated were collected by filtration to obtain 0.37 g (yield 95.8%) of D-α-(4-ethyl-2,3-dioxo-1-piperazinecarboxamido)-β-(S)-methoxybutyric acid having a melting point of 132° to 133° C.

(3) In 3 ml of anhydrous methylene chloride was suspended 0.18 g of the D-α-(4-ethyl-2,3-dioxo-1-piperazinecarboxamido)-β-(S)-methoxybutyric acid obtained in above (2), and thereto was added 0.1 g of oxalyl chloride. One drop of N,N-dimethylformamide was added to the suspension, and the temperature of the suspension was elevated to room temperature, after which the suspension was subjected to reaction for one hour. The reaction mixture was distilled under reduced pressure to remove the solvent, and the resulting residue was dissolved in 5 ml of anhydrous methylene chloride, after which to the resulting solution were added 0.28 g of diphenylmethyl 7β-amino-7α-methoxy-3-[5-(1-methyl-1,2,3,4-tetrazolyl)thiomethyl]-Δ³-cephem-4-carboxylate at −30° to −40° C., and then added 0.086 g of dimethylaniline. The resulting mixture was subjected to reaction at −20° to −10° C. for 12 hrs, and then distilled under reduced pressure to remove the solvent. The resulting residue was dissolved in a mixture of 5 ml of water and 10 ml of ethyl acetate. The organic layer was separated, washed with saturated aqueous sodium chloride solution, and then dried over anhydrous magnesium sulfate. The organic layer was distilled under reduced pressure to remove the solvent, and the resulting residue was purified by a column chromatography [Wako silica gel C-200; eluted with a mixture of benzene and ethyl acetate (1:1 by volume)] to obtain 0.28 g (yield 57.8%) of diphenylmethyl 7β-[D-α-(4-ethyl-2,3-dioxo-1-piperazinecarboxamido)-β-(S)-methoxybutanamido]-7α-methoxy-3-[5-(1-methyl-1,2,3,4-tetrazolyl(thiomethyl]-Δ³-cephem-4-carboxylate.

(4) In a mixture of 2 ml of anisole and 2 ml of trifluoroacetic acid was dissolved 0.18 g of the diphenylmethyl 7β-[D-α-(4-ethyl-2,3-dioxo-1-piperazinecarboxamido)-β-(S)-methoxybutanamido]-7α-methoxy-3-[5-(1-methyl-1,2,3,4-tetrazolyl)thiomethyl]-Δ³-cephem-4-carboxylate, and the solution was subjected to reaction for 30 min with ice-cooling. The reaction mixture was distilled under reduced pressure to remove the solvent, and to the resulting residue was added 10 ml of ethyl acetate, after which the mixture was stirred for 30 min. The crystals thus precipitated were collected by filtration to obtain 0.1 g (yield 70%) of 7β-[D-α-(4-ethyl-2,3-dioxo-1-piperazinecarboxamido)-β-(S)-methoxybutanamido]-7α-methoxy-3-[5-(1-methyl-1,2,3,4-tetrazolyl)thiomethyl]-Δ³-cephem-4-carboxylic acid having a melting point of 130° to 136° C. (decomp.).

IR (KBr) $cm^{-1}$: $\nu_{C=O}$ 1790, 1720–1680.

NMR ($CD_3COCD_3$: DMSO-$d_6$=4:1 by volume) δ values: 1.17 (3H, t, —$CH_3$), 1.23 (3H, d, —$CH_3$), 3.33 (3H, s, —$CH_3$), 3.45 (3H, s, —$CH_3$), 3.96 (3H, s, —CH₃), 3.25–4.60 (12H, m, >CH₂×5, >CH×2), 5.08 (1H, s, >CH), 8.97 (1H, s, >NH), 9.31 (1H, d, >NH).

In the same manner as above, the following compounds were obtained:

7β-[D-α-(4-ethyl-2,3-dioxo-1-piperazinecarboxamido)-β-(S)-ethoxybutanamido]-7α-methoxy-3-[5-(1-methyl-1,2,3,4-tetrazolyl)thiomethyl]-Δ³-cephem-4-carboxylic acid, m.p., 110° to 119° C. (decomp).

IR (KBr) cm⁻¹: $\nu_{C=O}$ 1780, 1720–1670.

NMR (CD₃COCD₃: DMSO-d₆=4:1 by volume) δ values: 1.10–1.35 (9H, m, —CH₃×3), 3.50 (3H, s, —CH₃), 3.98 (3H, s, —CH₃), 3.30–4.70 (14H, m, >CH₂×6, >CH×2), 5.03 (1H, s, >CH), 8.95 (1H, s, >NH), 9.40 (1H, d, >NH). 7β-[D-α-(4-ethyl-2,3-dioxo-1-piperazinecarboxamido)-β-(S)-tert.-butoxybutanamido]-7α-methoxy-3-[5-(1-methyl-1,2,3,4-tetrazolyl)thiomethyl]-Δ³-cephem-4-carboxylic acid, m.p., 110° to 115° C. (decomp.)

IR (KBr) cm⁻¹: $\nu_{C=O}$ 1780, 1730–1680.

NMR (CD₃COCD₃) δ values: 0.82–1.42 (15H, m, —CH₃×5), 3.50 (3H, s, —CH₃), 3.94 (3H, s, —CH₃), 3.22–4.58 (12H, m, >CH₂×5, >CH×2), 5.04 (1H, s, >CH), 8.48 (1H, s, >NH), 9.40 (1H, d, >NH).

EXAMPLE 9

(1) To 0.5 g of D-α-(4-ethyl-2,3-dioxo-1-piperazinecarboxamido)-β-(S)-hydroxybutyric acid was added 5 ml of formic acid, and the resulting mixture was subjected to reaction at 50° C. for 2 hrs, after which the reaction mixture was distilled under reduced pressure to remove the solvent. To the resulting residue was added 5 ml of ethyl acetate, and the crystals thus precipitated were collected by filtration to obtain 0.45 g (yield 82%) of D-α-(4-ethyl-2,3-1-dioxo-1-piperazinecarboxamido)-β-(S)-formyloxybutyric acid having a melting point of 170° to 175° C.

IR (KBr) cm⁻¹: $\nu_{C=O}$ 1740–1710, 1660.

NMR (DMSO-d₆) δ values: 1.15 (3H, t, —CH₃), 1.35 (3H, d, —CH₃), 3.10–3.72 (4H, m, >CH₂×2), 3.72–4.10 (2H, m, >CH₂), 4.40–4.70 (1H, m, >CH), 5.28–5.64 (1H, m, >CH),

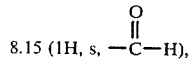
8.15 (1H, s, —C(=O)—H), 9.41 (1H, d, >NH).

(2) In 5 ml of anhydrous methylene chloride was suspended 0.3 g of D-α-(4-ethyl-2,3-dioxo-1-piperazinecarboxamido)-β-(S)-formyloxybutyric acid, and 0.14 g of oxalyl chloride was added to the suspension with ice-cooling, after which one drop of dimethylformamide was added thereto. The temperature of the suspension was elevated to room temperature, and the suspension was subjected to reaction for 30 min. The reaction mixture thus obtained was distilled under reduced pressure to remove the solvent. The resulting residue was dissolved in 5 ml of anhydrous methylene chloride, and the solution was cooled to −40° C. To the solution was added 0.45 g of diphenylmethyl 7β-amino-7α-methoxy-3-[5-(1-methyl-1,2,3,4-tetrazolyl)-thiomethyl]-Δ³-cephem-4-carboxylate, after which 0.12 ml of N,N-dimethylaniline was added thereto. The resulting mixture was subjected to reaction at −20° C. overnight. The reaction mixture was distilled under reduced pressure to remove the solvent, and 10 ml of water and 20 ml of ethyl acetate were added to the resulting residue to dissolve the latter, after which the organic layer was separated, washed with saturated aqueous sodium chloride solution, and then dried over anhydrous magnesium sulfate, and thereafter distilled under reduced pressure to remove the solvent. The resulting residue was purified by a column chromatography [Wako silica gel C-200; eluted with a mixture of chloroform and acetone (10:1 by volume)] to obtain 0.5 g (yield 64%) of diphenylmethyl 7β-[D-α-(4-ethyl-2,3-dioxo-1-piperazinecarboxamido)-β-(S)-formyloxybutanamido]-7α-methoxy-3-[5-(1-methyl-1,2,3,4-tetrazolyl)thiomethyl]-Δ³-cephem-4-carboxylate.

(3) In a mixture of 2 ml of anisole and 2 ml of trifluoroacetic acid was dissolved 0.2 g of diphenylmethyl 7β-[D-α-(4-ethyl-2,3-dioxo-1-piperazinecarboxamido)-β-(S)-formyloxybutanamido]-7α-methoxy-3-[5-(1-methyl-1,2,3,4-tetrazolyl)thiomethyl]-Δ³-cephem-4-carboxylate, and the resulting solution was subjected to reaction for 15 min with ice-cooling. The reaction mixture was distilled under reduced pressure to remove the solvent, and 10 ml of ethyl acetate was added to the resulting residue, after which the resulting mixture was stirred for 30 min. The crystals thus precipitated were collected by filtration to obtain 0.15 g (yield 94%) of 7β-[D-α-(4-ethyl-2,3-dioxo-1-piperazinecarboxamido)-β-(S)-formyloxybutanamido]-7α-methoxy-3-[5-(1-methyl-1,2,3,4-tetrazolyl)thiomethyl]-Δ³-cephem-4-carboxylic acid having a melting point of 147° to 155° C. (decomp.).

IR (KBr) cm⁻¹: $\nu_{C=O}$ 1780, 1720–1680.

NMR (DMSO-d₆) δ values: 0.90–1.35 (6H, m, —CH₃×2), 3.20–3.80 (6H, m, >CH₂×3), 3.40 (3H, s, —CH₃), 3.80–4.10 (2H, m, >CH₂), 3.94 (3H, s, —CH₃), 4.20–4.40 (2H, m, >CH₂), 4.50–4.90 (1H, m, >CH), 5.07 (1H, s, >CH), 5.20–5.50 (1H, m, >CH),

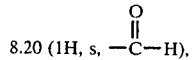
8.20 (1H, s, —C(=O)—H), 9.43 (1H, s, >NH), 9.54 (1H, d, >NH).

In the same manner as above the following compound was obtained:

7β-[D-α-(4-ethyl-2,3-dioxo-1-piperazinecarboxamido)-β-(S)-acetoxybutanamido]-7α-methoxy-3-[5-(1-methyl-1,2,3,4-tetrazolyl)thiomethyl]-Δ³-cephem-4-carboxylic acid, m.p., 136° to 142° C. (decomp.).

NMR (CD₃COCD₃: DMSO-d₆=4:1 by volume) δ values: 1.06–1.35 (6H, m, —CH₃×2), 2.01 (3H, s, —CH₃), 3.45 (3H, s, —CH₃), 3.98 (3H, s, —CH₃), 3.35–5.00 (12H, m, >CH₂×5, >CH×2), 5.02 (1H, s, >CH), 9.37 (1H, s, >NH), 9.45 (1H, d, >NH).

EXAMPLE 10

(1) In 20 ml of anhydrous methylene chloride was suspended 0.5 g of 7β-[D-α-(4-ethyl-2,3-dioxo-1-piperazinecarboxamido)-β-(S)-hydroxybutanamido]-3-[5-(1-methyl-1,2,3,4-tetrazolyl)thiomethyl]-Δ³-cephem-4-carboxylic acid, after which 0.76 ml of 2,3-dihydropyran and 0.021 g of pyridinium p-toluenesulfonate were added to the suspension. The resulting mixture was refluxed for 2 hrs. After the completion of the reaction, the reaction mixture was cooled to −75° C., and 1.5 ml of a lithium methoxide solution in methanol (3.725 mM of lithium methoxide was contained therein), after which the resulting mixture was subjected to reaction for 3 min. To the reaction mixture was added 0.123 ml of tert.-butyl hypochlorite, and the mixture was subjected to reaction for 15 min. To the reaction mixture was added 0.12 ml of formic acid, and the temperature of the mixture was elevated to room temperature, after which the mixture was distilled under reduced pressure to remove the solvent. The resulting residue was dissolved in a mixture of 10 ml of water and 10 ml of ethyl acetate, after which the pH of the solution was adjusted to 7.5 with a dilute aqueous sodium hydrogen carbonate solution. The aqueous layer was separated, and 10 ml of ethyl acetate was added thereto, after which the pH thereof was adjusted to 1.5 with 2 N hydrochloric acid with ice-cooling. The organic layer was separated therefrom, washed with water and saturated aqueous sodium chloride solution in this order, and then dried over anhydrous sodium sulfate. The organic layer was distilled under reduced pressure to remove the solvent, and diethyl ether was added to the residue, after which the crystals thus precipitated were collected by filtration to obtain 0.42 g (yield 70.6%) of 7β-[D-α-(4-ethyl-2,3-dioxo-1-piperazinecarboxamido)-β-(S)-(2-tetrahydropyranyloxy)butanamido]-7α-methoxy-3-[5-(1-methyl-1,2,3,4-tetrazolyl)thiomethyl]-Δ³-cephem-4-carboxylic acid having a melting point of 132° C. (decomp.).

IR (KBr) cm⁻¹: $\nu_{C=O}$ 1770, 1710–1670.

NMR (CDCl₃+D₂O) δ values: 1.20 (3H, t, —CH₃), 1.25 (3H, d, —CH₃), 1.4–1.9 (6H, m >CH₂×3), 3.52 (3H, s, —CH₃), 3.89 (3H, s, —CH₃), 3.5–4.9 (15H, m, >CH₂×6, >CH×3), 4.98 (1H, s, >CH).

(2) In 10 ml of 20% hydrous acetone was dissolved 0.5 g of 7β-[D-α-(4-ethyl-2,3-dioxo-1-piperazinecarboxamido)-β-(S)-(2-tetrahydropyranyloxy)butanamido]-7α-methoxy-3-[5-(1-methyl-1,2,3,4-tetrazolyl)thiomethyl]-Δ³-cephem-4-carboxylic acid, after the pH of the solution was adjusted to 0.5 with 6 N hydrochloric acid. The solution was subjected to reaction at room temperature for 2 hrs with stirring, after which the reaction mixture was distilled under reduced pressure to remove the solvent. The resulting residue was dissolved in a mixture of 8 ml of acetonitrile and 2 ml of saturated aqueous sodium chloride solution, and the organic layer was then separated. The aqueous layer was extracted with two 4-ml portions of acetonitrile, and the two extract acetonitrile layers were combined with the above organic layer. The combined organic layer was dried over anhydrous sodium sulfate and then distilled under reduced pressure to remove the solvent. To the resulting residue was added 7 ml of acetone, and the resulting mixture was stirred sufficiently, after which the crystals thus precipitated were collected by filtration, to obtain 0.4 g of the acetone adduct of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid. This was suspended in 2.4 ml of 20% hydrous acetone, and the pH thereof was adjusted to 5.0 with sodium hydrogen carbonate, after which 40 mg of active carbon was added thereto. The resulting mixture was stirred for 3 to 4 min, and then filtered through celite to remove the active carbon. The pH of the filtrate was then adjusted to 1.5 with 6 N hydrochloric acid, and the filtrate was stirred for 30 min at room temperature and thereafter stirred for 3 hrs with ice-cooling. The crystals thus precipitated were collected by filtration to obtain 0.32 g (yield 68.7%) of 7β-[D-α-(4-ethyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid dihydrate having a melting point of 173° to 175° C. (decomp.).

IR (KBr) cm⁻¹: $\nu_{C=O}$ 1775, 1710, 1675, 1660.

NMR (DMSO-d₆) δ values: 1.10 (3H, t, —CH₃), 1.15 (3H, d, —CH₃), 3.40 (3H, s, —CH₃), 3.93 (3H, s, —CH₃), 3.5–4.0 (8H, m, >CH₂×4), 4.1–4.4 (4H, m, >CH₂, >CH×2), 5.03 (1H, s, >CH), 9.2 (2H, d, >NH×2).

PHARMACEUTICAL PREPARATION EXAMPLE 1

Sodium bicarbonate was added to 7β-[D-α-(4-ethyl-2,3-dioxo-1-piperazinecarboxamido)-β-(S)-hydroxybutanamido]-7α-methoxy-3-[5-(1-methyl-1,2,3,4-tetrazoyl)thiomethyl]-Δ³-cephem-4-carboxylic acid, and the resulting mixture was treated in the conventional manner to obtain sodium salt which had been freeze-dried and sterilized. In 20 ml of saline solution was dissolved 1 g of said sodium salt in terms of potency to obtain an injection.

PHARMACEUTICAL PREPARATION EXAMPLE 2

In 3 ml of 0.5% (W/V) aqueous lidocaine hydrochloride solution was dissolved 1 g, in terms of potency, of the same compound as in Pharmaceutical Preparation Example 1, to obtain an injection.

PHARMACEUTICAL PREPARATION EXAMPLE 3

In 20 ml of 5% aqueous glucose solution was dissolved 1 g, in terms of potency, of the same compound as in Pharmaceutical Preparation Example 1 to obtain an injection.

In the same manner as in Pharmaceutical Preparation Example 1, freeze-dried sodium salts of other compounds could be obtained, and injections could be obtained from the salts.

What is claimed is:

1. A 7α-methoxycephalosporin or salt thereof, said 7α-methoxycephalosporin being represented by the formula:

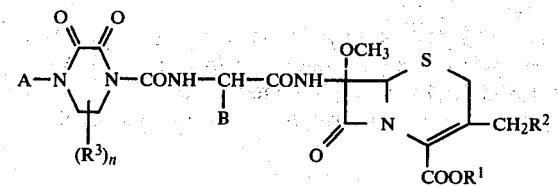

wherein
R' represents a hydrogen atom or a carboxyl-protecting group;
R² represents a substituted or unsubstituted lower alkoxy, lower alkylthio, C₁₋₁₀ acyloxy, carbamoyloxy or heterocyclic thio group in which the thio linkage is attached to a carbon atom of a 5 or 6 membered aromatic heterocyclic ring composed of carbon and at least one hetero atom selected from oxygen, sulfur and nitrogen, the heterocyclic moiety of said heterocyclic thio group being composed of said aromatic heterocyclic ring or of said aromatic heterocyclic ring fused to a benzene ring or being triazolopyridyl, purinyl, or pyridine-1-oxide-2-yl, the substituent of the substituted group being selected from a halogen, lower alkyl, phenyl, C₂₋₅ alkenyl, hydroxyl, lower alkoxy, lower alkylthio, nitro, cyano, lower alkylamino, di-lower alkylamino, $C_{1-10}$ acylamino, $C_{1-10}$ acyl, $C_{1-10}$ acyloxy, $C_{1-10}$ acyl-lower alkyl, carboxyl, carbamoyl, amino-lower alkyl, N-lower alkylamino-lower alkyl, N,N-di-lower alkyl-amino-lower alkyl, hydroxy-lower alkyl, hydroxyimino-lower alkyl, lower alkoxy-lower alkyl, carboxy-lower alkyl, sulfo-lower alkyl, sulfo, sulfamoyl-lower alkyl, sulfamoyl, carbamoyl-lower alkyl, carbamoyl-$C_{2-5}$ alkenyl, and N-hydroxycarbamoyl-lower alkyl;

$R^3$ represents a lower alkyl group;

n is 0, 1 or 2;

A represents a hydrogen atom or a straight- or branched-chain $C_{1-14}$ alkyl group which is unsubstituted or substituted with a halogen, lower alkoxy, cyano, nitro, carboxyl, lower alkoxycarbonyl, hydroxyl, lower alkylthio or $C_{1-10}$ acyl group; and B represents a straight- or branched-chain $C_{1-14}$ alkyl group which is unsubstituted or substituted with a halogen, hydroxyl, protected hydroxyl, $C_{1-10}$ acyl, mercapto, lower alkylthio, nitro, amino, protected amino, imino, protected imino or carboxyl group.

2. A 7α-methoxycephalosporin or a salt thereof according to claim 1, wherein A represents a hydrogen atom or a lower alkyl group; B represents a $C_{1-4}$ alkyl group which is substituted by hydroxyl, protected hydroxyl or halogen; and n is 0.

3. A 7α-methoxycephalosporin or a salt thereof according to claim 2, wherein $R^2$ represents an acetoxy group or a substituted or unsubstituted 5-(1,2,3,4-tetrazolyl)thio or 2-(1,3,4-thiadiazolyl)thio group.

4. A 7α-methoxycephalosporin or a salt thereof according to claim 3, wherein B represents

5. 7β-[D-α-(4-ethyl-2,3-dioxo-1-piperazinecarboxamido)-β-(S or R)-hydroxybutanamido]-7α-methoxy-3-[5-(1-methyl-1,2,3,4-tetrazolyl)thiomethyl]-Δ³-cephem-4-carboxylic acid or a pharmaceutically acceptable salt thereof.

6. 7β-[D-α-(4-ethyl-2,3-dioxo-1-piperazinecarboxamido)-β-hydroxypropionamido]-7α-methoxy-3-[5-(1-methyl-1,2,3,4-tetrazolyl)thiomethyl]-Δ³-cephem-4-carboxylic acid or its pharmaceutically acceptable salt.

7. 7β-[D-α-(4-ethyl-2,3-dioxo-1-piperazinecarboxamido)-propionamido]-7α-methoxy-3-[5-(1-methyl-1,2,3,4-tetrazolyl)thiomethyl]-Δ³-cephem-4-carboxylic acid or its pharmaceutically acceptable salt.

8. 7β-[DL-α-(4-ethyl-2,3-dioxo-1-piperazinecarboxamido)-α-(chloromethyl)acetamido]-7α-methoxy-3-[5-(1-methyl-1,2,3,4-tetrazolyl)thiomethyl]-Δ³-cephem-4-carboxylic acid or its pharmaceutically acceptable salt.

9. 7β-[D-α-(4-ethyl-2,3-dioxo-1-piperazinecarboxamido)-β-(S)-hydroxybutanamido]-7α-methoxy-3-[5-(1-β-hydroxyethyl-1,2,3,4-tetrazolyl)thiomethyl]-Δ³-cephem-4-carboxylic acid or its pharmaceutically acceptable salt.

10. 7β-[D-α-(4-ethyl-2,3-dioxo-1-piperazinecarboxamido-β-(S)-hydroxybutanamido]-7α-methoxy-3-acetoxymethyl-Δ³-cephem-4-carboxylic acid or its pharmaceutically acceptable salt.

11. 7β-[D-α-(4-ethyl-2,3-dioxo-1-piperazinecarboxamido)-β-(S)-hydroxybutanamido]-7α-methoxy-3-[2-(1,3,4-thiadiazolyl)thiomethyl]-Δ³-cephem-4-carboxylic acid or its pharmaceutically acceptable salt.

12. 7β-[D-α-(4-n-butyl-2,3-dioxo-1-piperazinecarboxamido)-β-(S)-hydroxybutanamido]-7α-methoxy-3-[5-(1-methyl-1,2,3,4-tetrazolyl)thiomethyl]-Δ³-cephem-4-carboxylic acid or its pharmaceutically acceptable salt.

13. 7β-[D-α-(4-ethyl-2,3-dioxo-1-piperazinecarboxamido)-β-(S)-methoxybutanamido]-7α-methoxy-3-[5-(1-methyl-1,2,3,4-tetrazolyl)thiomethyl]-Δ³-cephem-4-carboxylic acid or its pharmaceutically acceptable salt.

14. 7β-[D-α-(4-ethyl-2,3-dioxo-1-piperazinecarboxamido)-β-(S)-formyloxybutanamido]-7α-methoxy-3-[5-(1-methyl-1,2,3,4-tetrazolyl)thiomethyl]-Δ³-cephem-4-carboxylic acid or its pharmaceutically acceptable salt.

15. A pharmaceutical composition useful for treating bacteria infections in man and mammals which comprises an antibacterially effective amount of a compound or its pharmaceutically acceptable salt as claimed in claim 1, in combination with a pharmaceutically acceptable inert diluent or carrier.

16. A pharmaceutical composition according to claim 15, wherein the 7α-methoxycephalosporin or its pharmaceutically acceptable salt is 7β-[D-α-(4-ethyl-2,3-dioxo-1-piperazinecarboxamido)-β-(S or R)-hydroxybutanamido]-7α-methoxy-3-[5-(1-methyl-1,2,3,4-tetrazolyl)thiomethyl]-Δ³-cephem-4-carboxylic acid or its pharmaceutically acceptable salt.

* * * * *